United States Patent
Arora et al.

(10) Patent No.: US 10,902,442 B2
(45) Date of Patent: Jan. 26, 2021

(54) MANAGING ADOPTION AND COMPLIANCE OF SERIES PURCHASES

(71) Applicant: INTERNATIONAL BUSINESS MACHINES CORPORATION, Armonk, NY (US)

(72) Inventors: Parul Arora, New York, NY (US); Raphael Ezry, New York, NY (US); Munish Goyal, Yorktown Heights, NY (US); Jingzi Tan, Chicago, IL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 926 days.

(21) Appl. No.: 15/251,440

(22) Filed: Aug. 30, 2016

(65) Prior Publication Data
US 2018/0060889 A1    Mar. 1, 2018

(51) Int. Cl.
*G06Q 30/02* (2012.01)
*G16H 40/20* (2018.01)

(52) U.S. Cl.
CPC ..... *G06Q 30/0203* (2013.01); *G06Q 30/0201* (2013.01); *G06Q 30/0204* (2013.01); *G16H 40/20* (2018.01)

(58) Field of Classification Search
None
See application file for complete search history.

(56) References Cited

U.S. PATENT DOCUMENTS

| | | | |
|---|---|---|---|
| 5,974,396 A | 10/1999 | Anderson et al. | |
| 6,970,830 B1 | 11/2005 | Samra et al. | |
| 7,003,476 B1 | 2/2006 | Samra et al. | |
| 7,050,753 B2 | 5/2006 | Knutson | |
| 7,424,439 B1 | 9/2008 | Fayyad et al. | |
| 7,743,059 B2 | 6/2010 | Chan et al. | |
| 7,996,253 B2 | 8/2011 | Reed et al. | |
| 8,521,579 B2 | 8/2013 | Witting | |
| 9,070,140 B2 | 6/2015 | Allard et al. | |
| 9,639,848 B1 * | 5/2017 | Belle | G06Q 30/0202 |

(Continued)

FOREIGN PATENT DOCUMENTS

| | | |
|---|---|---|
| WO | 2008121872 A1 | 10/2008 |
| WO | 2016013972 A1 | 1/2016 |

OTHER PUBLICATIONS

Vijay Mahajan, Eitan Muller, and Frank M. Bass, "Diffusion of New Products: Empirical Generalizations and Managerial Uses," Marketing Science 14(3) (1995), pp. G79-G88 (Year: 1995).*

(Continued)

*Primary Examiner* — Jan P Mincarelli

(74) *Attorney, Agent, or Firm* — James Nock, Esq.; Hye Jin Lucy Song, Esq.; Heslin Rothenberg Farley & Mesiti P.C.

(57) ABSTRACT

Methods, computer program products, and systems are presented. The methods include, for instance: identifying a target customer population of a series product and dividing into segments by customer behaviors relevant to adoption of and compliance to a series of purchases of the series product. A marketing campaign strategy for each segment is devised and executed, and adoption rate and compliance rate is predicted by analytical modeling and later evaluated by actual sales data. Parameters used in predicting the adoption rate and the compliance rate are adjusted for accuracy.

17 Claims, 7 Drawing Sheets

(56) References Cited

U.S. PATENT DOCUMENTS

| | | | |
|---|---|---|---|
| 2007/0178433 A1 | 8/2007 | Leonard et al. | |
| 2008/0065462 A1 | 3/2008 | Yamamoto et al. | |
| 2009/0113008 A1* | 4/2009 | Gonzalez | G06F 19/3456 709/206 |
| 2009/0307057 A1* | 12/2009 | Azout | G06Q 30/02 705/7.29 |
| 2010/0100418 A1 | 4/2010 | Richter et al. | |
| 2010/0211456 A1* | 8/2010 | Reed | G06Q 10/0637 705/14.43 |
| 2013/0218678 A1 | 8/2013 | Benyamin et al. | |
| 2014/0372175 A1 | 12/2014 | Jain et al. | |
| 2014/0379473 A1 | 12/2014 | Zhou et al. | |
| 2015/0142521 A1 | 5/2015 | Aydin et al. | |
| 2015/0163311 A1* | 6/2015 | Heath | G06Q 30/0201 709/204 |
| 2015/0242862 A1 | 8/2015 | Rupple et al. | |

OTHER PUBLICATIONS

"Strategies to Achieve the Healthy People 2020 Annual Influenza Vaccine Coverage Goal for Health-Care Personnel: Recommendations from the National Vaccine Advisory Committee" Public Health Rep. Jan.-Feb. 2013; 128(1): 7-25. [retrieved Aug. 30, 2016]. Retrieved from the Internet <URL: http://www.ncbi.nlm.nih.gov/pmc/articles/PMC3514716/pdf/phr128000007.pdf>, 2013, 19 pgs.

"Effectiveness of interventions that apply new media to improve vaccine uptake and vaccine coverage: A systematic review", Hum Vaccin Immunother. Jan. 2015; 11(1): 72-82), [retrieved on Aug. 30, 2016]. Retrieved from the Internet <URL: http://www.ncbi.nlm.nih.gov/pmc/articles/PMC4514191/pdf/khvi-11-01-984112.pdf>, published online Aug. 7, 2014, doi: 10,4161/hv,34313, 11 pgs.

Salathe, Marcel, et al., "Assessing Vaccination Sentiments with Online Social Media: Implications for Infectious Disease Dynamics and Control", Center for Infectious Disease Dynamics, Department of Biology, Penn State University, [retrieved on Aug. 12, 2016]. Retrieved from the Internet <URL: https://arxiv.org/ftp/arxiv/papers/1105/1105.4502.pdf>, 27 pgs.

Huesch, Marco, et al., "Vaccination (Anti-) Campaigns in Social Media", Expanding the Boundaries of Health Informatics Using Artificial Intelligence: Papers from the AAAI 2013 Workshop, [retrieved on Aug. 12, 2016]. Retrieved from the Internet <URL: www.aaai.org/ocs/index.php/WS/AAAIW13/paper/viewFile/7094/6502>, 4 pgs.

Rao, Neel, et al., "Social Networks and Vaccination Decisions", Federal Reserve Bank of Boston, No. 07-12, [retrieved on Aug. 12, 2016]. Retrieved from the Internet <URL: file:///C:/Users/spl/Downloads/wp0712.pdf>, 50 pgs.

Pawlicki, Michael, "Cluster Analysis—a market segmentation procedure", [retrieved on Aug. 25, 2016]. Retrieved from the Internet <URL: http://michaelpawlicki.com/cluster-analysis/>, Jan. 8, 2013, 3 pgs.

Mell, Peter, et al., "The NIST Definition of Cloud Computing", NIST Special Publication 800-145, Sep. 2011, Gaithersburg, MD, 7 pgs.

* cited by examiner

EQ410
$$f(t) = \left[p + \frac{q}{N}N(t)\right][1 - F(t)]$$

EQ420
$$C = \sum_{t=0}^{lim} c_i x_i$$

MANAGING ADOPTION AND COMPLIANCE OF SERIES PURCHASES

TECHNICAL FIELD

The present disclosure relates to predictive modeling and analytics, and more particularly to methods, computer program products, and systems for predicting and managing consumer behaviors of adoption and compliance in series purchases.

BACKGROUND

Conventional marketing campaign strategies for conventional mass media are shifting to information gathering and targeted marketing by use of social media. For products that should be purchased in a number of times, knowledge on consumers regarding purchase behavior may be utilized for a more effective marketing campaigns.

SUMMARY

The shortcomings of the prior art are overcome, and additional advantages are provided, through the provision, in one aspect, of a method. The method for managing a series purchase includes, for example: obtaining, by one or more processor of a computer, customer data and social media data relevant to purchases of a series product, wherein the series product is a type of product that needs to be purchased more than once for a customer to maximize a benefit from the product; identifying a target customer population by use of the customer data; dividing the target customer population into more than one segment based on behavioral characteristics of a group of target customers that are relevant to adoption and compliance of the series product; devising a marketing strategy for a segment of the more than one segment and executing the marketing strategy to the segment; estimating an adoption rate of the series product by use of an analytical model; predicting a compliance rate of the series product by use of the analytical model; evaluating the adoption rate and the compliance rate by use of a sales data; and adjusting parameters of the analytical model such that the adoption rate and the compliance rate would better resemble the sales data.

Additional features are realized through the techniques set forth herein. Other embodiments and aspects, including but not limited to computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 4 depicts formulae to predict adoption rate and compliance rate of a series product, in accordance with one or more embodiments set forth herein;

DETAILED DESCRIPTION

Figure 1:
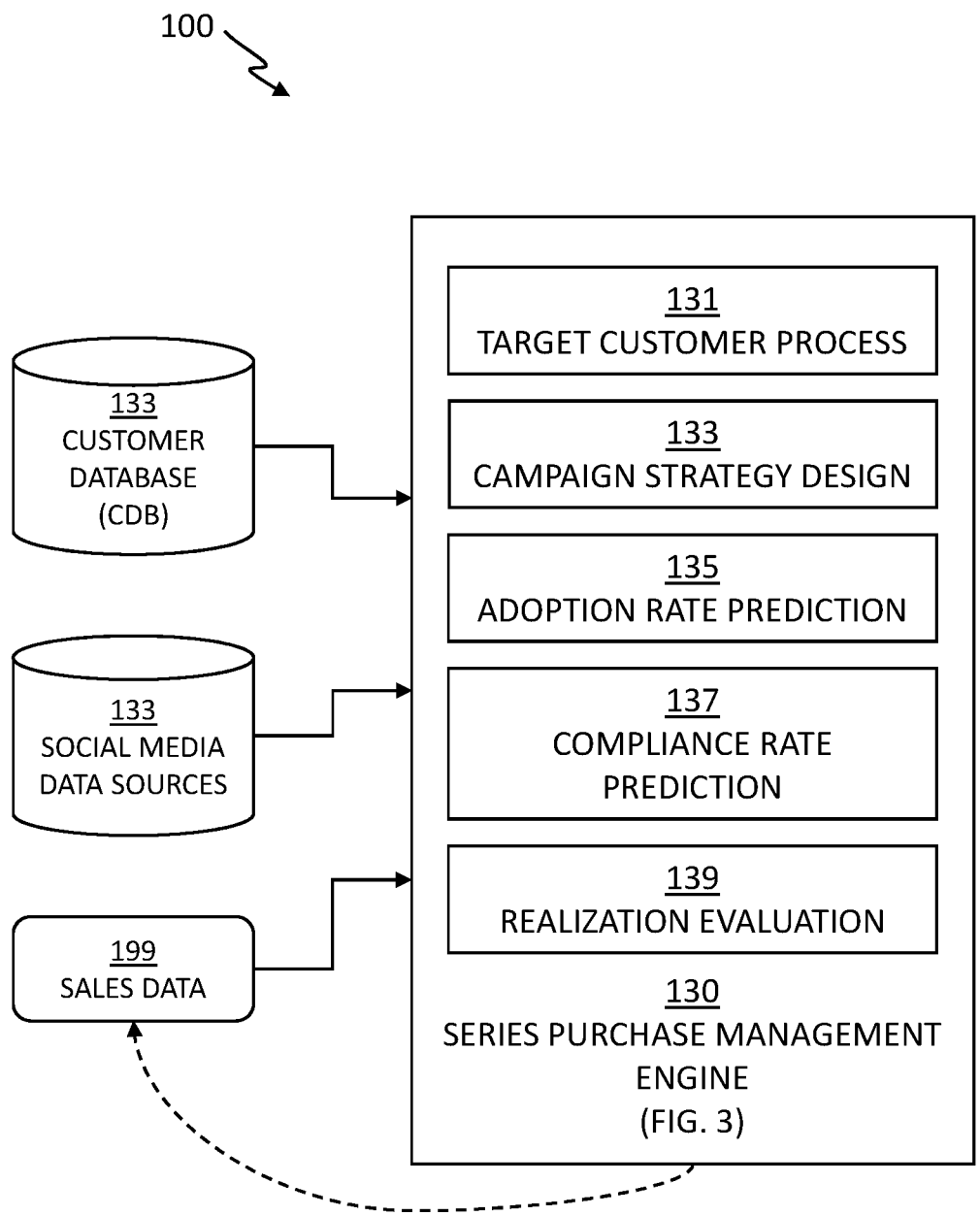
FIG. 1 depicts a system 100 for managing series purchases, in accordance with one or more embodiments set forth herein.

FIG. 1 depicts a system 100 for managing series purchases, in accordance with one or more embodiments set forth herein.

The system 100 for managing series purchases includes a series purchase management engine 130 that obtains data from a customer database (CDB) 110, social media data sources 120, and sales data 199.

The series purchase management engine 130 concerns a class of products which requires consumers to purchase more than one product in an orderly fashion to benefit from the products. For example, a vaccination should be performed in multiple separate doses over a period of time, and unless patients gets all doses as requested by the vaccination regime, the patients would not become immune to a disease. For another example, an education program offering a recognizable certificate or a degree upon completion of a certificate program specifying a certain number of credits to be earned, a student does not get benefit from taking courses in the program until the student makes purchases for the specified number of courses for the certificate/degree. Also, in the same example, if the student wishes to take an advanced course, the student is required to purchase all prerequisite courses of the advanced course. Still another example, a loyalty program of airlines and hotels would require subsequent purchases and a certain cumulated purchase amount for any award of benefits and discounts, and if a consumer signs up for the loyalty program with a first purchase but does not go back for more purchases, there would be no benefit for the consumer in signing up.

Because whether or not consumers who made a first purchase will follow through with subsequent purchases is uncertain, providers of the class of products requiring a series of purchases may need to predict how the consumers would behave with the subsequent purchases, and if possible, may want to assist the consumers to complete the series purchases. In this specification, the first purchase of the series of purchases is referred to as adoption, and a subsequent purchase toward completion of the series The series purchase management engine 130 includes of a target customer process 131, a campaign strategy design process 133, an adoption rate prediction process 135, a compliance rate prediction process 137, and a realization evaluation process 139. The components 131, 133, 135, 137, and 139 of the series purchase management engine 130 are abstracted functional components, and may or may not be implemented as an individual component, depending on embodiments of the present invention. The target customer process 131 identifies and analyzes population cohorts to capture a network effect, also referred to as a word-of-mouth effect, population dynamics, and effects of marketing effort. The adoption rate prediction process 135 utilizes Bass diffusion model to predict future adoption among the population cohorts, and predicts a dynamic adoption rate of a series product. Detailed operations of the series purchase management engine 130 are presented in FIG. 3 and corresponding description.

Figure 2:
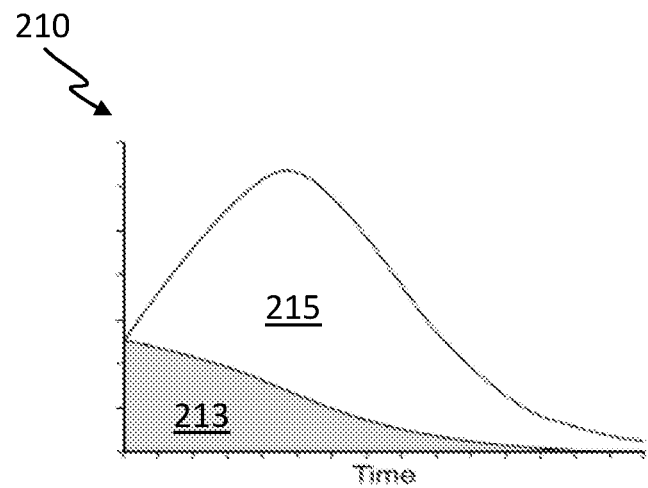
FIG. 2 depicts graphs regarding interested consumer behaviors of adoption and compliance of series purchases, in accordance with one or more embodiments set forth herein.
Figure 2:
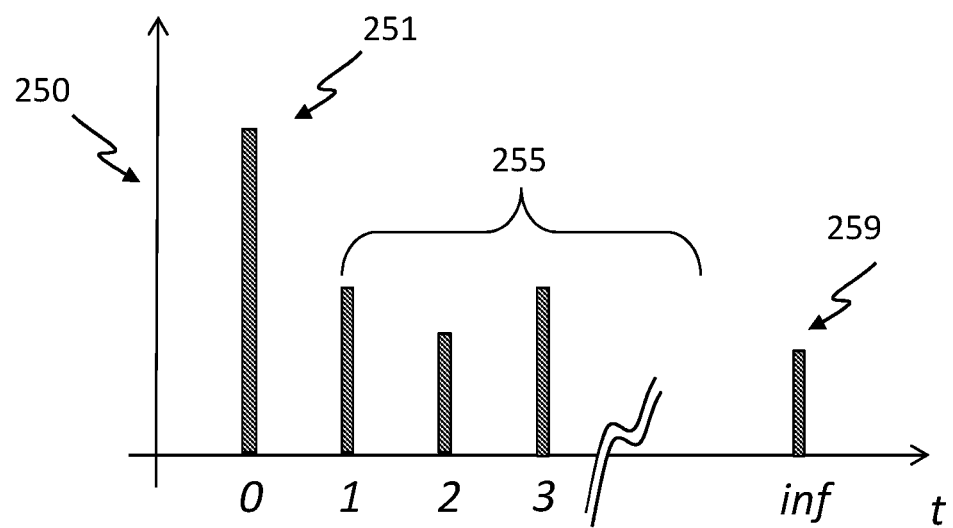

FIG. 2 depicts graphs regarding interested consumer behaviors of adoption and compliance of series purchases, in accordance with one or more embodiments set forth herein.

Graph 210 represents how a composition of new adopters based on customer behavior changes over time. When a product launches at zero point of the graph, innovators represented by area 213 is most of the new adopters as shown. The innovators are a type of customers who venture into and purchase the product regardless of how well the product is received. Ares 215 represents imitators who make a purchase if the product is well-received by the customers who already purchased the product. A target customer population may be a combination of the new adopters and non-adopters, and the new adopters may be a combination of the innovators and the imitators. A likelihood of adoption at time t is estimated by formula EQ410 of FIG. 4. Details of formula EQ410 are presented in block 340 of FIG. 3 and corresponding description.

Graph 250 represents how compliance rate is evaluated. A first bar 251 at time t=0 represents a number of adopters, that is, customers who purchase a first product from a series product. A group of bars 255 in the middle from t=1 and t=(inf−1), represents respective number of customers who keep purchasing a next product in the series product until t. A last bar 259 at time t=inf represents a number of adopters who have not made any subsequent purchase from the series product. The compliance rate is evaluated by use of the number of customers in respective bars 251, 255, and 259, as presented in formula EQ420 of FIG. 4. Details of formula EQ420 are presented in block 350 of FIG. 3 and corresponding description.

Figure 3:
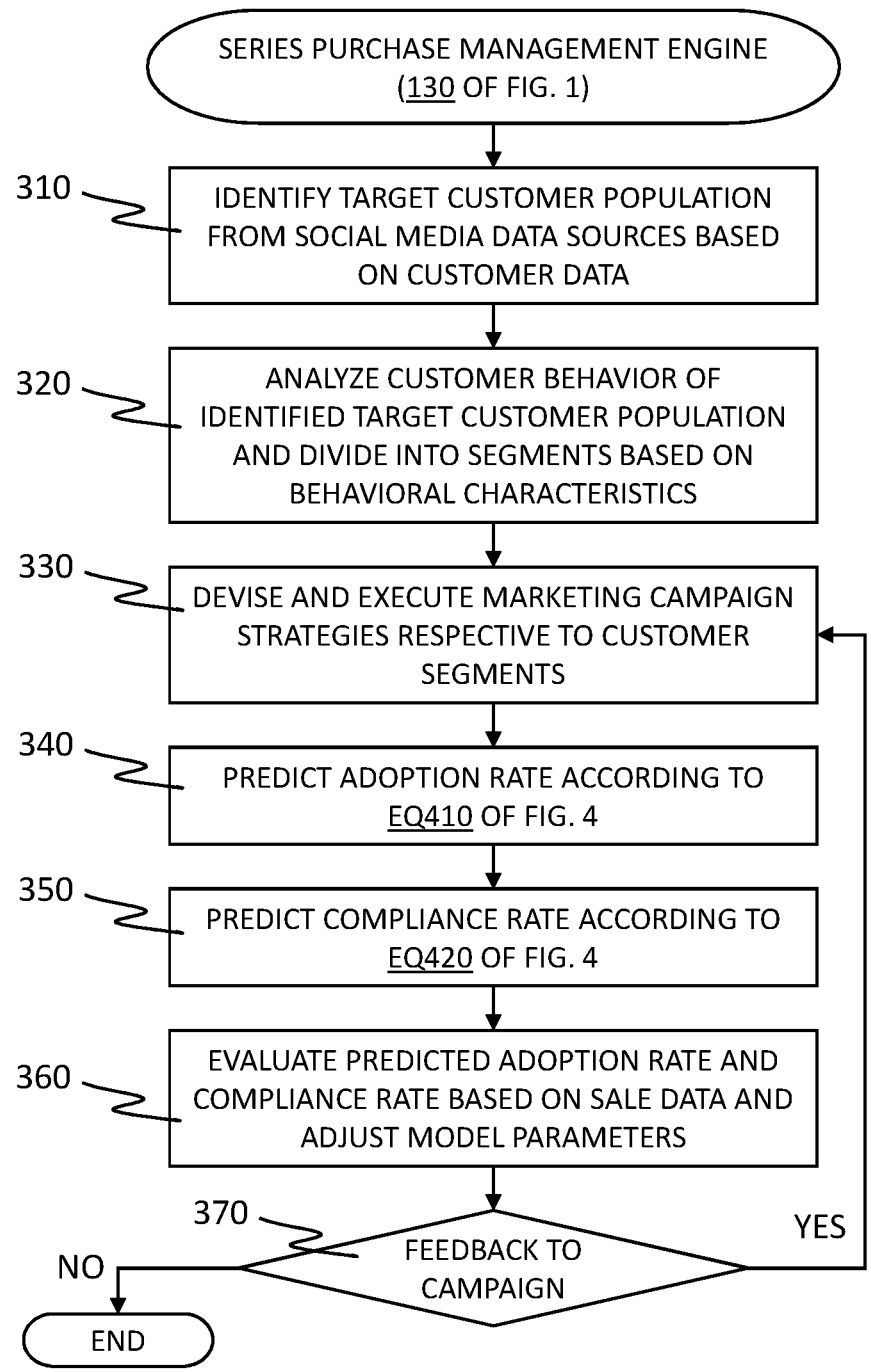
FIG. 3 depicts a flowchart for the series purchase management engine, in accordance with one or more embodiments set forth herein.

FIG. 3 depicts a flowchart for the series purchase management engine 130 of FIG. 1, and FIG. 4 depicts formulae to predict adoption rate and compliance rate of a series product, in accordance with one or more embodiments set forth herein.

The series purchase management engine 130 operates in two-phases. Blocks 310 through 330 are in a first phase in which the series purchase management engine 130, by use of the target customer process 131 and a campaign strategy design process 133, identifies likely customers of a series product and promotes an adoption of the series product as well as a compliance to a regime of the series product, based on data from the customer database (CDB) 110 and the social media data sources 120. Blocks 340 through 360 are in a second phase in which the series purchase management engine 130, by use of the adoption rate prediction process 135, the compliance rate prediction process 137, and the realization evaluation process 139, predicts a rate of the adoption and a rate of the compliance according to modeled formulation embodiments of the present invention, and evaluates the predicted rates based on the sales data 199 that is deemed consequential to marketing campaigns devised in the first phase. Pursuant to the realization result, marketing campaign strategies may be optimized for respective target customer segments by use of repeated feedback and adjustment cycles.

In block 310, the series purchase management engine 130 identifies a target customer population of a series product from the social media data sources 120 based on the CDB 110. The target customer population is determined by attributes of age, gender, geographical location, areas of interest, etc., for which the series product is made. Then the series purchase management engine 130 proceeds with 320.

In block 320, the series purchase management engine 130, analyzes customer behaviors of the target customer population identified from block 310 and divide the target customer population into target customer segments by behavioral characteristics. The series purchase management engine 130 looks for indicators as to how disciplined, forgetful, punctual, persistent, and otherwise rule-abiding, individual customers may be such that a marketing campaign is devised appropriately for each target customer segment in order to optimize compliance and to maximize overall sales. Then the series purchase management engine 130 proceeds with 330.

In block 330, the series purchase management engine 130 devises respective marketing strategy for each target customer segment, and executes the respective marketing strategies for the target customer segments. Examples of marketing strategies may be, but not limited to, calling the customers, texting/emailing the customers, sending a reminder letter to the customers, etc. The series purchase management engine 130 subsequently gathers sales data attributable to the marketing strategies. Then the series purchase management engine 130 proceeds with 340.

In block 340, the series purchase management engine 130 predicts the adoption rate according to formula EQ410 of FIG. 4. As noted in graph 210 of FIG. 2, the target customer population may be a combination of new adopters and non-adopters, and the new adopters may be a combination of innovators and imitators. The adoption rate $$f(t) = \left[p + \frac{q}{N}N(t)\right][1 - F(t)]$$

as in formula EQ410 of FIG. 4 is a function of time t, wherein p is a coefficient of innovation that represents the innovators amongst the new adopters, N(t) is a number of customers who already adopted at time t, N is the total market potential (N>0), q is a coefficient of imitation, and F(t) is a cumulative function of the adoption rate ƒ(t). In formula EQ410, a second argument $$\frac{q}{N}N(t)$$

represents the imitators amongst the new adopters. Coefficients p and q are estimated based on a type of products. For a pharmaceutical series product such as a sequential vaccination, p is estimated based on features of the product that may attract the innovators such as efficacy, safety, competition, price, etc., and q is estimated based on features of the product that may attract the imitators such as recommendations by doctors, patient reviews, etc. For other retail products, p is estimated based on features such as property, quality, price, newness, etc., and q is estimated based on features such as publicity, comments from evaluation agencies, comments by product experts, and user review, etc. Then the series purchase management engine 130 produces the predicted adoption rate to a user and proceeds with 350.

In block 350, the series purchase management engine 130 predicts the compliance rate according to EQ420 of FIG. 4, which is formulated by building a probabilistic model by machine learning to capture various behaviors of the customers that are relevant to the compliance. An example of customer behavior that is relevant to the compliance may be, among other things, forgetting. In certain embodiments of the present invention wherein the series purchase consists of multiple number of purchases of an identical product, the series purchase management engine 130 builds and utilizes the probabilistic model that isolates subsequent purchases contributing to the compliance rate from an initial purchases contributing to the adoption rate. The series purchase management engine 130 then predicts the compliance rate as a ratio of returning customers for subsequent purchases and when the returning customers makes the subsequent purchases.

As noted in descriptions of graph 250, the number of adopters and respective number of subsequent customers who make purchases from t=1 and t=(inf−1), as well as a number of adopters who have not made any subsequent purchase from the series product within a reasonable period of time from the first purchase are either acquired from the sales data 199 or predicted by the probabilistic model for the compliance rate.

The number of compliant customers $C=\Sigma_{t=1}^{lim} c_i x_i$ as in formula EQ420 of FIG. 4 is a sum of respective number of subsequent customers who make purchases from the time after an initial purchase until a compliance cutoff, wherein $x_i$ represents a number of compliant customers who make a subsequent purchase at time i, $c_i$ represents a coefficient for each time unit indicating delay factors and intervals between purchases, and lint represents the compliance cutoff which is a reasonable period of time within which an adopted customer may return for a subsequent purchase. The bar 259, graph 250 of FIG. 2, at time t=inf, represents a number of opt-out customers who have not made any subsequent purchase from the series product. The number of adopters is a sum of the number of compliant customers C and the number of opt-out customers. The compliance rate is a ratio of the number of compliant customers C to the number of adopters at time 0. Then the series purchase management engine 130 produces the predicted compliance rate to the user and proceeds with 360.

In block 360, the series purchase management engine 130 evaluates the adoption rate predicted in block 340 and the compliance rate predicted in block 350 based on the sales data 199 and adjusts model parameters from EQ410 and EQ420 to optimize the accuracy of the predictions. Then the series purchase management engine 130 proceeds with 370.

In block 370, the series purchase management engine 130 determines whether or not to give feedback to block 330 of marketing strategy for a revision based on the a realization of the marketing campaign strategies based on the sales data 199. If the series purchase management engine 130 determines that the marketing strategies need to be updated with the sales data feedback, then the series purchase management engine 130 loops back to block 330. If the series purchase management engine 130 determines that the marketing strategies are optimized, then the series purchase management engine 130 terminates.

Certain embodiments of the present invention may offer various technical computing advantages, including building a probabilistic model by machine learning for analyzing consumer behavior relevant to adoption and compliance of series products. The adoption and compliance rates are modeled based on the consumer behavior and adoption and compliance dynamics in a market for series products. Further, by use of iterative method, parameters used in predicting the adoption and compliance rates are adjusted to ensure more accurate prediction of the adoption and compliance rates. Further, marketing strategies designed for respective target customer segments are optimized over time by use of feedbacks from sales data and realization evaluation.

FIGS. 5-8 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
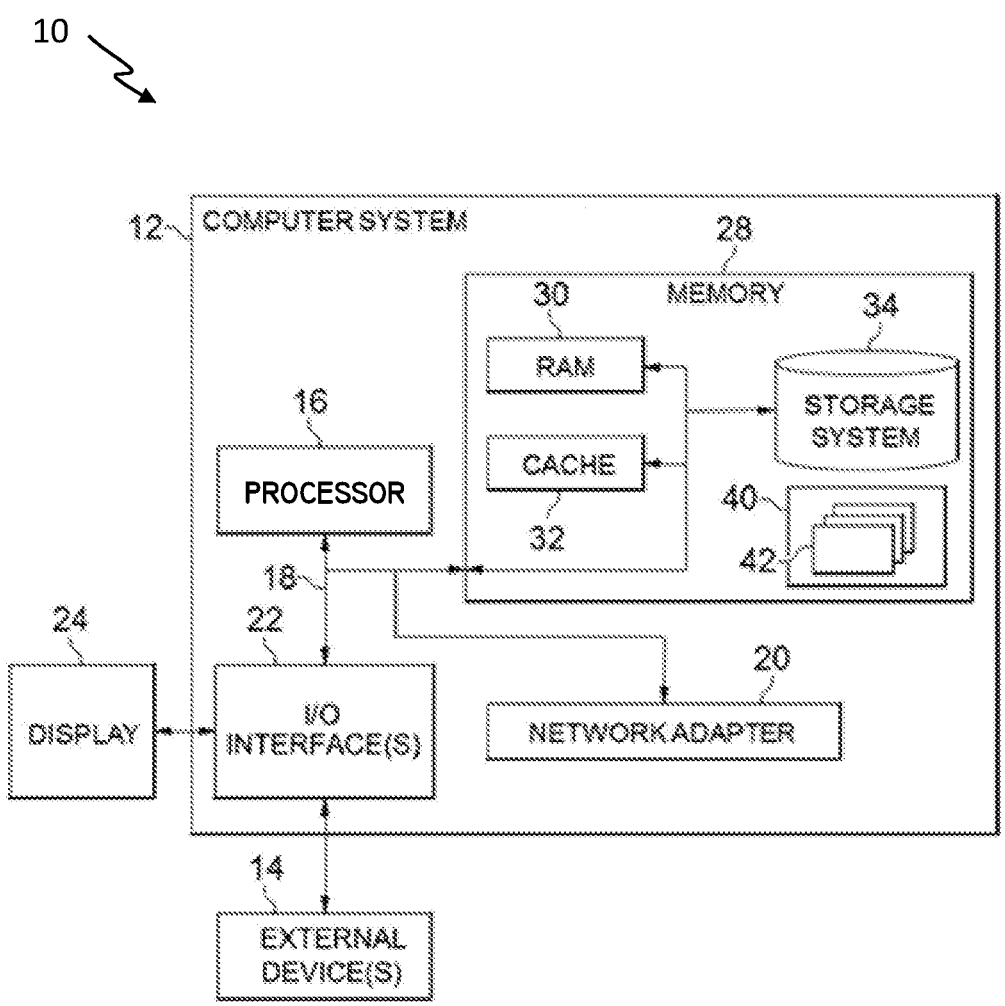
FIG. 5 depicts a cloud computing node according to an embodiment of the present invention.

Referring now to FIG. 5, a schematic of an example of a computer system/cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 5, computer system 12 in cloud computing node 10 is shown in the form of a general-purpose computing device. The components of computer system 12 may include, but are not limited to, one or more processors 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. Each of the operating system, one or more application programs, other program processes, and program data or some combination thereof, may include an implementation of the series purchase management engine 130 of FIG. 1. Program processes 42, as in the flowchart of FIG. 3, describing processes of the series purchase management engine 130, generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc.

Figure 6:
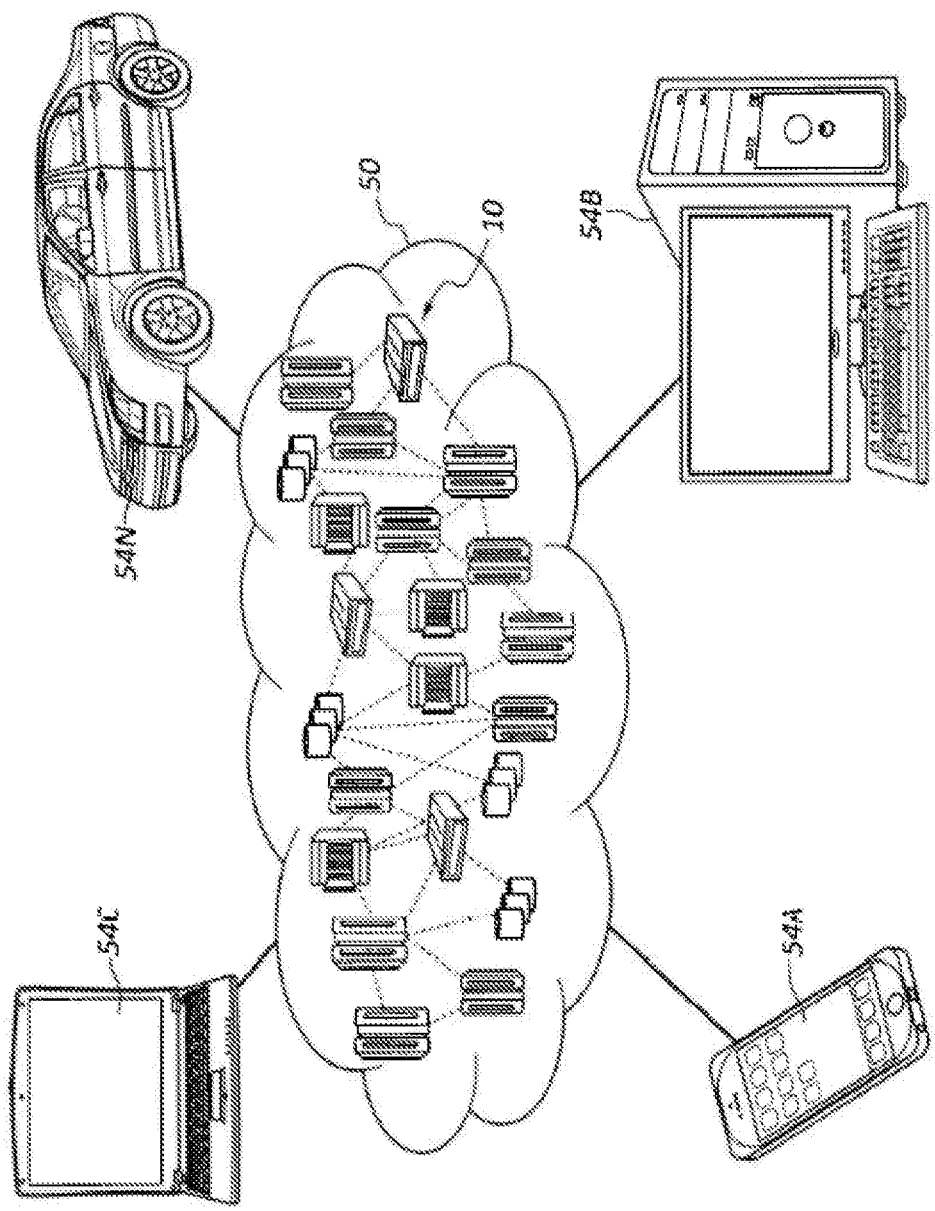
FIG. 6 depicts a cloud computing environment according to an embodiment of the present invention.

Referring now to FIG. 6, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 running one or more instances of the series purchase management engine 130 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
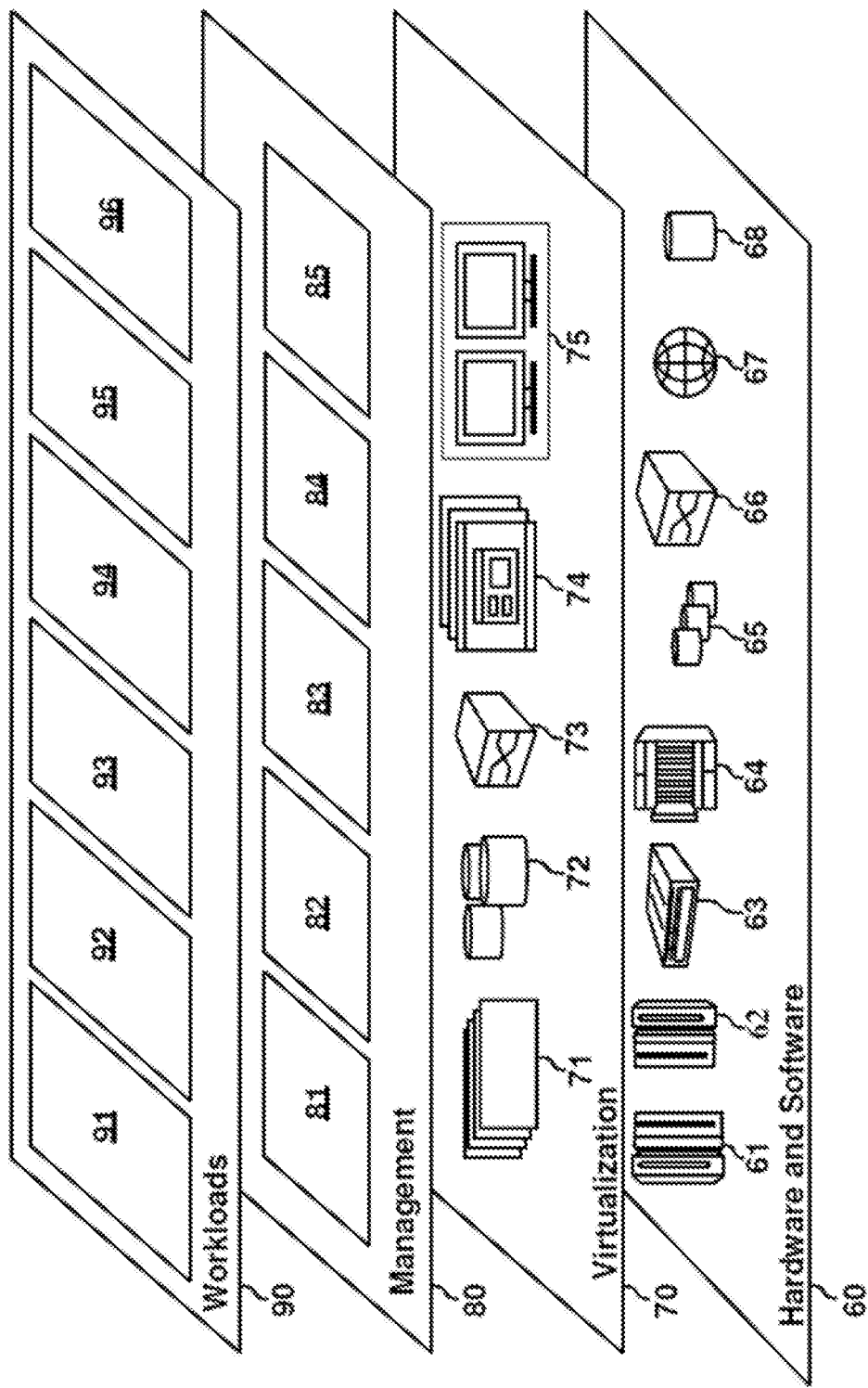
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components for the series purchase management engine 96, as described herein. The processing components 96 can be understood as one or more program 40 described in FIG. 5.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method, comprising:
  obtaining, by one or more processor of a computer, customer data and social media data relevant to purchases of a series product, wherein the series product is a type of product that needs to be purchased more than once for a customer to maximize a benefit from a product;
  identifying, by the one or more processor, a target population with respect to the series product by use of the social media data and the customer data;
  estimating, by the one or more processor, an adoption rate of the series product by use of an analytical model of adoption, wherein the adoption rate of the series product indicates a ratio of adopters who make a first purchase of the series product amongst the target population, comprising:
    calculating the adoption rate as a function of time, denoted as $f(t)$, having a first component representing a ratio of innovators amongst the adopters, a second component representing a number of customers who already adopted at time t, a third component representing a ratio of imitators amongst the adopters at time t, and a fourth component representing a cumulative function of the adoption rate at time t, wherein the adoption rate is modeled as a function of time t, wherein p denotes the first component, N(t) denotes the second component, qN(t)/N denotes the third component, and F(t) denotes the fourth component, wherein p is estimated based on features of the series product appealing to the innovators, and wherein q is estimated based on features of the series product appealing to the imitators, and wherein the series product is a retail product, wherein p is estimated based on the features appealing to the innovators comprising property, quality, newness, and price, and wherein q is estimated based on factors appealing to the imitators comprising publicity, comments from evaluation agencies, comments by product experts, and user review;

predicting, by the one or more processor, a compliance rate of the series product by use of a probabilistic model of compliance that captures behavioral characteristics of the target population relevant to a compliance by machine learning, wherein training parameters of the probabilistic model of compliance are based on respective behavioral characteristics per each segment of target population for training the probabilistic model of compliance, wherein the compliance rate of the series product indicates a ratio of compliant customers who make a subsequent purchase of the series product amongst the adopters, and wherein a number of adopters is from the estimating per each time unit;

producing, by the one or more processor, sales data of the series product;

evaluating, by the one or more processor, the compliance rate as produced by the probabilistic model of compliance, based on the sales data; and adjusting, by the one or more processor, the training parameters of the probabilistic model of compliance such that the compliance rate would better resemble the sales data.

2. A computer implemented method, comprising:

identifying, by one or more processor, a target population by attributes of the target population with respect to a series product, from social media data and customer data stored in customer database, wherein the series product is a type of product that needs to be purchased more than once in an orderly fashion for a customer to maximize a benefit from a product;

predicting, by the one or more processor, a compliance rate of the series product by use of a probabilistic model of compliance that captures behavioral characteristics of the target population relevant to a compliance and a completion of purchases of the series product by machine learning, wherein training parameters of the probabilistic model of compliance are based on respective behavioral characteristics per each segment of target population for training the probabilistic model of compliance, wherein the compliance rate of the series product indicates a ratio of compliant customers who make a subsequent purchase of the series product within a certain time limit amongst adopters who already made a first purchase of the series product in the target population;

evaluating, by the one or more processor, the compliance rate as produced by the probabilistic model of compliance, based on actual data of compliance by the target population; and adjusting, by the one or more processor, the training parameters of the probabilistic model of compliance as reflected in delay factors and intervals between purchases of the probabilistic model of compliances as accumulated for each time unit, to thereby improve an accuracy of the compliance rate from the predicting, wherein the adjusting is iteratively performed according to a result of the evaluating and a preconfigured accuracy of prediction from the predicting.

3. The computer implemented method of claim 2, wherein the series product is a pharmaceutical product, wherein a ratio of innovators amongst the adopters is estimated based on features comprising efficacy, safety, competition, and price, and wherein a ratio of imitators amongst the adopters at a certain point of time is estimated based on factors comprising recommendations by doctors and patient reviews.

4. The computer implemented method of claim 2, wherein the series product is a retail product, wherein a ratio of innovators amongst the adopters is estimated based on features comprising property, quality, newness, and price, and wherein a ratio of imitators amongst the adopters at a certain point of time is estimated based on factors comprising publicity, comments from evaluation agencies, comments by product experts, and user review.

5. The computer implemented method of claim 2, wherein the training parameters representing the behavioral characteristics of the target population relevant to the compliance modeled in the probabilistic model of compliance include discipline, forgetfulness, punctuality, persistence, and a rule-abiding characteristic.

6. The computer implemented method of claim 2, the predicting the compliance rate comprising:

cumulating, by use of the probabilistic model of compliance, a number of the compliant customers at each time unit multiplied by respective coefficients for compliance for the time unit, wherein the respective coefficients for compliance indicate delay factors and intervals between purchases of the series product.

7. The computer implemented method of claim 2, the predicting the compliance rate comprising:

calculating, by use of the probabilistic model of compliance, a number of the compliant customers, as a sum of respective numbers of subsequent customers who make subsequent purchases in each time unit after an initial purchase until a compliance cutoff, based on the behavioral characteristics of the target population that are relevant to the compliance as modeled in the probabilistic model of compliance per each time unit, wherein the compliance cutoff indicates the certain time limit within which an adopter can return for a subsequent purchase to be accounted as a compliance.

8. The computer implemented method of claim 1, further comprising:

building, prior to the predicting, the probabilistic model of compliance by machine learning on the behavioral characteristics relevant to indicators on completion of purchases of the series product for individual customers of the target population;

dividing the target population into more than one segment based on the behavioral characteristics of respective segments that are relevant to compliances of the series product as featured in the probabilistic model of compliance; and retraining the probabilistic model of compliance with respect to the training parameters representing the behavioral characteristics of respective segments of the target population based on actual data of compliance by the target population, subsequent to the evaluating, wherein the training parameters representing the behavioral characteristics of each segment of the target population relevant to the compliance modeled in the probabilistic model of compliance include discipline, forgetfulness, punctuality, and persistence.

9. The computer implemented method of claim 2, further comprising:

prior to the evaluating, collecting the actual data of compliance as produced by the target population over time for a preconfigured training period for the probabilistic model of compliance.

10. A computer program product comprising:

a computer readable storage medium readable by one or more processor and storing instructions for execution by the one or more processor for performing a method comprising:

identifying, by one or more processor, a target population by attributes of the target population with respect to a series product, from social media data and customer data stored in customer database, wherein the series product is a type of product that needs to be purchased more than once in an orderly fashion for a customer to maximize a benefit from a product;

predicting, by the one or more processor, a compliance rate of the series product by use of a probabilistic model of compliance that captures behavioral characteristics of the target population relevant to a compliance and a completion of purchases of the series product by machine learning, wherein training parameters of the probabilistic model of compliance are based on respective behavioral characteristics per each segment of target population for training the probabilistic model of compliance, wherein the compliance rate of the series product indicates a ratio of compliant customers who make a subsequent purchase of the series product within a certain time limit amongst adopters who already made a first purchase of the series product in the target population;

evaluating, by the one or more processor, the compliance rate as produced by the probabilistic model of compliance, based on actual data of compliance by the target population; and adjusting, by the one or more processor, the training parameters of the probabilistic model of compliance as reflected in delay factors and intervals between purchases of the probabilistic model of compliance as accumulated for each time unit, to thereby improve an accuracy of the compliance rate from the predicting, wherein the adjusting is iteratively performed according to a result of the evaluating and a preconfigured accuracy of prediction from the predicting.

11. The computer program product of claim 10, wherein the series product is a pharmaceutical product, wherein a ratio of innovators amongst the adopters is estimated based on features comprising efficacy, safety, competition, and price, and wherein a ratio of imitators amongst the adopters at a certain point of time is estimated based on factors comprising recommendations by doctors and patient reviews.

12. The computer program product of claim 10, wherein the series product is a retail product, wherein a ratio of innovators amongst the adopters is estimated based on features comprising property, quality, newness, and price, and wherein a ratio of imitators amongst the adopters at a certain point of time is estimated based on factors comprising publicity, comments from evaluation agencies, comments by product experts, and user review.

13. The computer program product of claim 10, wherein the training parameters representing the behavioral characteristics of the target population relevant to the compliance modeled in the probabilistic model of compliance include discipline, forgetfulness, punctuality, persistence, and a rule-abiding characteristic.

14. The computer program product of claim 10, the predicting the compliance rate comprising:

cumulating, by use of the probabilistic model of compliance, a number of the compliant customers at each time unit multiplied by respective coefficients for compliance for the time unit, wherein the respective coefficients for compliance indicate delay factors and intervals between purchases of the series product.

15. The computer program product of claim 10, the predicting the compliance rate comprising:

calculating, by use of the probabilistic model of compliance, a number of the compliant customers, as a sum of respective numbers of subsequent customers who make subsequent purchases in each time unit after an initial purchase until a compliance cutoff, based on the behavioral characteristics of the target population that are relevant to the compliance as modeled in the probabilistic model of compliance per each time unit, wherein the compliance cutoff indicates the certain time limit within which an adopter can return for a subsequent purchase to be accounted as a compliance.

16. The computer program product of claim 10, further comprising:

building, prior to the predicting, the probabilistic model of compliance by machine learning on the behavioral characteristics relevant to indicators on completion of purchases of the series product for individual customers of the target population;

dividing the target population into more than one segment based on the behavioral characteristics of respective segments that are relevant to compliances of the series product as featured in the probabilistic model of compliance; and retraining the probabilistic model of compliance with respect to the training parameters representing the behavioral characteristics of respective segments of the target population based on the actual data of compliance by the target population, subsequent to the evaluating, wherein the training parameters representing the behavioral characteristics of each segment of the target population relevant to the compliance modeled in the probabilistic model of compliance include discipline, forgetfulness, punctuality, and persistence.

17. The computer program product of claim 10, further comprising:

prior to the evaluating, collecting the actual data of compliance as produced by the target population over time for a preconfigured training period for the probabilistic model of compliance.

* * * * *